US011534341B2

(12) United States Patent
Li et al.

(10) Patent No.: US 11,534,341 B2
(45) Date of Patent: Dec. 27, 2022

(54) METHOD FOR PREPARING PERSONALIZED MEDICAL ISOLATION GOGGLES BY THREE-DIMENSIONAL (3D) PRINTING

(71) Applicants: Dongguan University of Technology, Dongguan (CN); Dongguan Songhu Technology Co., Ltd., Dongguan (CN); Institute of Science & Technology Innovation, Dongguan University of Technology, Dongguan (CN); Dongguan Keheng Hand Model Co., Ltd., Dongguan (CN)

(72) Inventors: Nan Li, Dongguan (CN); Zirong Zhou, Dongguan (CN); Shenggui Chen, Dongguan (CN); Binghua Wen, Dongguan (CN)

(73) Assignees: DONGGUAN UNIVERSITY OF TECHNOLOGY, Dongguan (CN); DONGGUAN SONGHU TECHNOLOGY CO., LTD., Dongguan (CN); INSTITUTE OF SCIENCE & TECHNOLOGY INNOVATION, DONGGUAN UNIVERSITY OF TECHNOLOGY, Dongguan (CN); DONGGUAN KEHENG HAND MODEL CO., LTD., Dongguan (CN)

( * ) Notice: Subject to any disclaimer, the term of this patent is extended or adjusted under 35 U.S.C. 154(b) by 21 days.

(21) Appl. No.: 17/039,174

(22) Filed: Sep. 30, 2020

(65) Prior Publication Data

US 2021/0259886 A1 Aug. 26, 2021

(30) Foreign Application Priority Data

Feb. 26, 2020 (CN) ........................ 202010118265.7

(51) Int. Cl.
*A61F 9/02* (2006.01)
*B33Y 10/00* (2015.01)
(Continued)

(52) U.S. Cl.
CPC .............. *A61F 9/02* (2013.01); *B29C 64/135* (2017.08); *B29C 64/35* (2017.08); *B29C 64/386* (2017.08);
(Continued)

(58) Field of Classification Search
CPC ..... B29C 64/124; B29C 64/135; B29C 64/35; B29C 64/386; B29C 64/393; B33Y 10/00; B33Y 40/20; B33Y 50/00; B33Y 50/02
See application file for complete search history.

(56) References Cited

U.S. PATENT DOCUMENTS

2008/0111816 A1* 5/2008 Abraham ............... B33Y 50/00 345/420
2015/0055085 A1* 2/2015 Fonte .................... G16H 50/50 700/98

(Continued)

FOREIGN PATENT DOCUMENTS

CN 108363218 8/2018

*Primary Examiner* — Nahida Sultana
(74) *Attorney, Agent, or Firm* — Cozen O'Connor

(57) ABSTRACT

A method for preparing a pair of personalized three-dimensional (3D) printing medical isolation goggles includes the steps of S1: establishing a medical isolation goggles matrix; S2: acquiring the facial data of a user; S3: establishing a personalized medical isolation goggles model; S4: performing additive manufacturing, wherein a pair of medical isolation goggles is provided with high personalized fitness and high breathability for patients with eye diseases such as conjunctivitis, virus-susceptible patients, front-line clinical medical workers and related workers, and the compression damage to the face caused by the wearing of the medical (Continued)

7 isolation goggles for a long time is reduced in terms of fitness and comfort, where the medical isolation goggles are manufactured in a mode of additive manufacturing, small-batch rapid production can be performed after data merging, and a large number of processes and costs are reduced in the production cycle.

8 Claims, 3 Drawing Sheets

(51) Int. Cl.

| | |
|---|---|
| ***B33Y 50/00*** | (2015.01) |
| ***B33Y 80/00*** | (2015.01) |
| ***B29C 64/386*** | (2017.01) |
| ***B29C 64/35*** | (2017.01) |
| ***B29C 64/135*** | (2017.01) |
| ***B33Y 40/20*** | (2020.01) |
| ***H04N 1/00*** | (2006.01) |
| ***B29K 75/00*** | (2006.01) |
| ***B29L 31/48*** | (2006.01) |

(52) U.S. Cl.
CPC ............... *B33Y 10/00* (2014.12); *B33Y 40/20* (2020.01); *B33Y 50/00* (2014.12); *B33Y 80/00* (2014.12); *H04N 1/00251* (2013.01); *B29K 2075/00* (2013.01); *B29L 2031/4807* (2013.01)

(56) References Cited

U.S. PATENT DOCUMENTS

| | | | | |
|---|---|---|---|---|
| 2017/0248802 | A1* | 8/2017 | Rasschaert | G02C 5/146 |
| 2018/0150993 | A1* | 5/2018 | Newell | H04N 5/00 |
| 2018/0281314 | A1* | 10/2018 | Littlefield | B33Y 50/02 |
| 2020/0215415 | A1* | 7/2020 | Bologna | B29C 64/393 |
| 2021/0145643 | A1* | 5/2021 | Jehanno | G02C 3/003 |
| 2021/0173230 | A1* | 6/2021 | Yang | B29C 64/393 |
| 2021/0346091 | A1* | 11/2021 | Haslam | G16H 10/60 |
| 2021/0401088 | A1* | 12/2021 | Lamoncha | A62B 18/082 |

* cited by examiner

METHOD FOR PREPARING PERSONALIZED MEDICAL ISOLATION GOGGLES BY THREE-DIMENSIONAL (3D) PRINTING

BACKGROUND OF THE INVENTION

1. Field of the Invention

The present invention relates to the technical field of three-dimensional (3D) printing, and in particular, to a method for preparing personalized medical isolation goggles by 3D printing.

2. Description of the Related Art

In the prior art, a goggles frame of a pair of medical isolation goggles is formed by an injection molding process, and the final product is obtained after annealing. Patent No. CN108363218A discloses a pair of goggles and a preparation method thereof. The method includes taking ET311X polycarbonate as the main material and taking ABS and TR90 as auxiliaries, melting and mixing the main material and the auxiliaries to obtain a stable molten mixed solution, and filtering and performing injection molding and annealing to obtain a goggles frame. The method has the disadvantages that the injection molding is adopted, so that the pair of medical isolation goggles is only distinguished in size, and does not take the fit for a facial feature size into account. This makes polluted gas, spittle and other tiny objects enter the pair of medical isolation goggles easily.

SUMMARY OF THE INVENTION

In view of the foregoing, is an object of the invention to provide a method for preparing personalized medical isolation goggles by 3D printing that solves the foregoing problems associated with the prior art, such that a pair of medical isolation goggles closely fit a user, and pollutants are prevented from entering the medical isolation goggles.

This and other objects and advantages are achieved in accordance with the invention by a method for preparing personalized medical isolation goggles by 3D printing, including the following steps:

S1: establishing a medical isolation goggles matrix: performing 3D scanning on a basic tester to obtain point cloud data from front and side faces of the basic tester's face, and performing 3D design on the obtained data to obtain the medical isolation goggles matrix;

S2: acquiring facial data of a user: photographing the user or performing 3D scanning on the user to obtain point cloud data from front and side faces of the user's face;

S3: establishing a personalized medical isolation goggles model: importing the point cloud data of the medical isolation goggles matrix in S1 and the point cloud data of the user in S2 into 3D software for Boolean operations, and forming, by merging and cutting, a personalized medical isolation goggles model conforming to the user's face; and S4: performing additive manufacturing: importing the personalized medical isolation goggles model into slice software matched with a 3D printer to perform 3D model slicing, generating a print format file which can be identified by the 3D printer, and inputting the print format file into the 3D printer to print the personalized medical isolation goggles model to obtain a pair of personalized medical isolation goggles.

Preferably, during 3D scanning, the basic tester sits down naturally with eyes closed, high-precision 3D data of the basic tester's face is quickly acquired by using a hand-held 3D scanner, and the point cloud data of the basic tester's face is converted into triangular mesh surface data in software of the 3D scanner.

Preferably, the 3D software is Solid Works or Autodesk Maya.

Preferably, Boolean operations are performed in accordance with the nose, brow ridge, and forehead in the scanning data of the user and the medical isolation goggles matrix.

Preferably, the personalized medical isolation goggles model is saved in "Standard Triangle Language" or "Standard Tessellation Language" (STL) format.

Preferably, 3D printing is performed by a thermoplastic polyurethane (TPU) material and a stereolithography appearance (SLA) technology.

Preferably, the method further includes a step S5 of post-processing assembly specifically as follows: A pair of personalized medical isolation goggles is cleaned and ground to remove unnecessary supports and post-cured and sterilized, a layer of sponge pad is stuck to a curved nose bracket of the pair of personalized medical isolation goggles, medical isolation goggles laces penetrate into medical isolation goggles lace openings at rear ends of both sides of the pair of personalized medical isolation goggles, high transmittance lenses are embedded in a goggles frame at a front end of the pair of personalized medical isolation goggles, both sides of a medical isolation goggles frame body of the pair of personalized medical isolation goggles are provided with several air holes, filter cotton is placed in a filter cotton placement bracket at the periphery of the air holes, and finally a pair of finished personalized medical isolation goggles is obtained.

Preferably, the medical isolation goggles lace is an elastic band, and a buckle is arranged at a joint of the elastic band.

The present invention achieves the following technical effects compared with the prior art.

The present invention provides a pair of medical isolation goggles with high personalized fitness and high breathability for patients suffering from eye diseases such as conjunctivitis, virus-susceptible patients, front-line clinical medical workers and related workers, and the compression damage to the face caused by the wearing of the medical isolation goggles for a long time is reduced in terms of fitness and comfort. The medical isolation goggles are manufactured in a mode of additive manufacturing. Small-batch rapid production can be performed after data merging, and a large number of processes and costs are reduced in the production cycle.

Other objects and features of the present invention will become apparent from the following detailed description considered in conjunction with the accompanying drawings. It is to be understood, however, that the drawings are designed solely for the purpose of illustration and not as a definition of the limits of the invention, for which reference should be made to the appended claims. It should be further understood that the drawings are necessarily drawn to scaler and that, unless indicated, they are merely intended to conceptually illustrate the structures and procedures described herein.

BRIEF DESCRIPTION OF THE DRAWINGS

To describe the technical solutions in the examples of the present invention or in the prior art more clearly, the following briefly introduces the accompanying drawings required for describing the examples. Apparently, the accompanying drawings in the following description show merely some examples of the present invention, and a person of ordinary skill in the art may still derive other accompanying drawings from these accompanying drawings without creative efforts, in which.

DETAILED DESCRIPTION OF THE EXEMPLARY EMBODIMENTS

The following clearly and completely describes the technical solutions in the examples of the present invention with reference to accompanying drawings in the examples of the present invention. It should be apparent, the described examples are merely some rather than all of the examples of the present invention. All other examples obtained by a person of ordinary skill in the art based on the examples of the present invention without creative efforts shall fall within the protection scope of the present invention.

Figure 1:
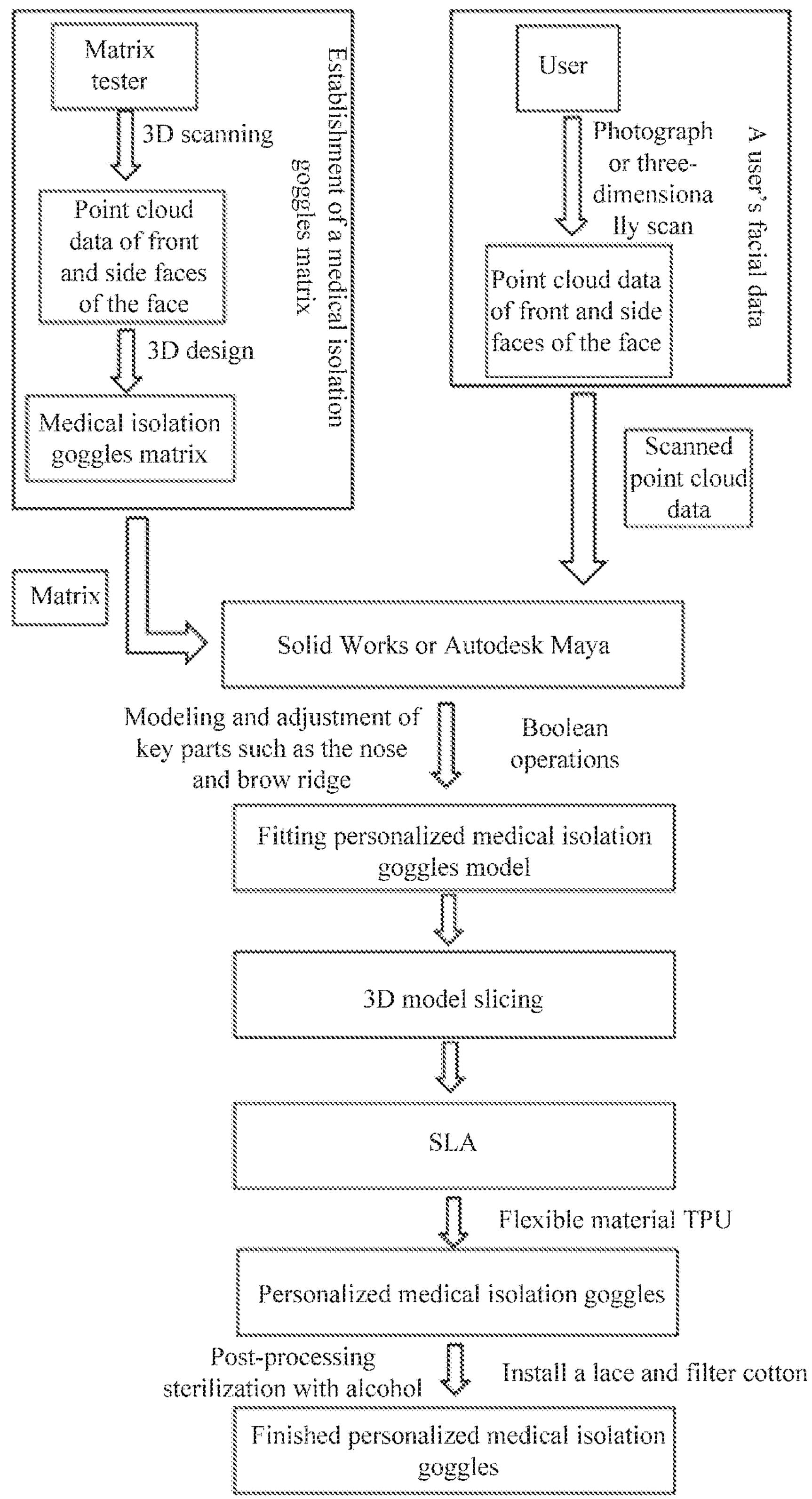
FIG. 1 is a flowchart of a method for preparing personalized medical isolation goggles by 3D printing in accordance with the invention.
Figure 2:
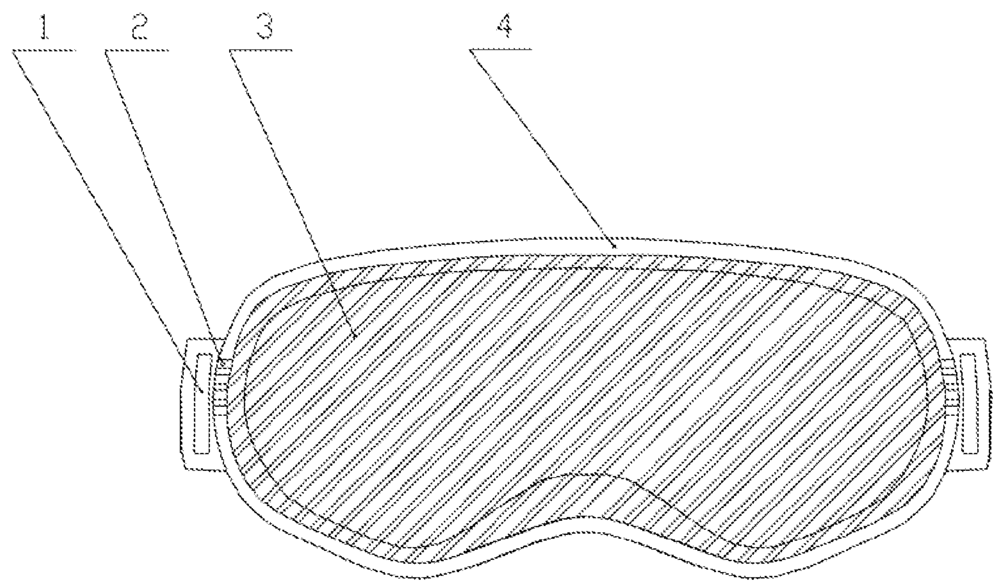
FIG. 2 is a front view of the pair of personalized medical isolation goggles accordance with the present invention.
Figure 3:
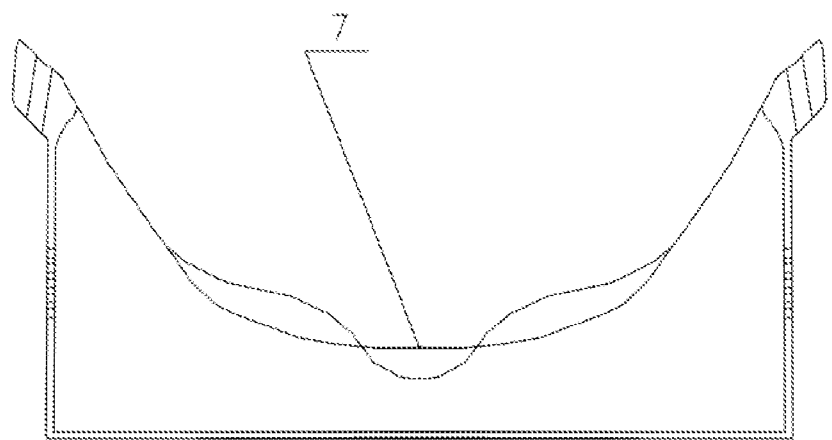
FIG. 3 is a top view of the pair of personalized medical isolation goggles accordance with the present invention.
Figure 4:
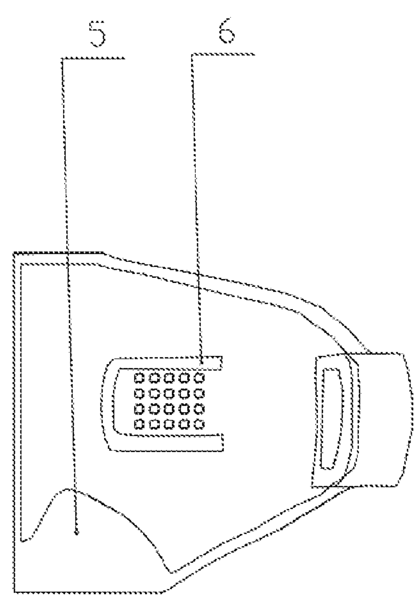
FIG. 4 is a side view of the pair of personalized medical isolation goggles accordance with the present invention.

With reference to FIGS. 2-2, shown therein is medical isolation goggles lace opening 1, air holes 2, high transmittance lens 3, medical isolation goggles frame body 4, curved nose bracket 5, filter cotton placement bracket 6, and sponge pad 7.

The present invention provides a method for preparing personalized medical isolation goggles by 3D printing to solve the foregoing problems in the prior art, such that the pair of medical isolation goggles highly fits a user, and pollutants are prevented from entering the medical isolation goggles.

In order to make the foregoing objectives, features, and advantages of the present invention more understandable, the present invention will be further described in detail below with reference to the accompanying drawings and specific examples.

As shown in FIGS. 1-4, this example provides a method for preparing personalized medical isolation goggles by 3D printing, including the following steps.

S1: establishing a medical isolation goggles matrix: perform 3D scanning on a basic tester to obtain point cloud data from front and side faces of the basic tester's face, and perform 3D design on the obtained data to obtain the medical isolation goggles matrix. Preferably, during 3D scanning, the basic tester sits down naturally with eyes closed, high-precision 3D data of the basic tester's face is quickly acquired by using a hand-held 3D scanner, and the point cloud data of the basic tester's face is converted into triangular mesh surface data in software of the 3D scanner. The 3D scanner can convert, in accordance with stereo information of a real object, the data into digital signals that can be directly processed by a computer, and the point cloud generated is more uniform. Therefore, the accuracy is higher and the stability is higher.

S2: acquiring of facial data of user: photograph the user or perform 3D scanning on the user to obtain point cloud data from front and side faces of the user's face.

S3: establishing a personalized medical isolation goggles model: import the point cloud data of the medical isolation goggles matrix in S1 and the point cloud data of the user in S2 into 3D software for Boolean operations, where the Boolean operations include merging, cutting, and intersecting; and form, by merging and cutting, a personalized medical isolation goggles model conforming to the user's face. Preferably, the 3D software is Solid Works or Autodesk Maya. The Boolean operations are performed in accordance with key parts (such as the nose, brow ridge and forehead) in the scanning data of the user and the medical isolation goggles matrix. The personalized medical isolation goggles model is saved in STL format.

S4: performing additive manufacturing: import the personalized medical isolation goggles model into slice software matched with a 3D printer to perform 3D model slicing, generate a print format file that can be identified by the 3D printer, and input the print format file into the 3D printer to print the personalized medical isolation goggles model, where 3D printing is specifically performed by a thermoplastic polyurethane (TPU) material and a stereolithography appearance (SLA) technology, so as to obtain a pair of personalized medical isolation goggles. In one edition, 25 pairs of personalized medical isolation goggles can be printed simultaneously, which greatly shortens the printing time and achieves the purpose of rapid customized production.

This example further includes a step S5 of post-processing assembly specifically as follows. The pair of personalized medical isolation goggles by 3D printing is moved to a post-processing area by a mechanical hand. The pair of personalized medical isolation goggles is cleaned and ground to remove unnecessary supports (air hole supports) and post-cured and sterilized, and the sterilization is specifically performed with medicinal alcohol. A layer of sponge pad 7 is stuck to a curved nose bracket 5 of the pair of personalized medical isolation goggles, and medical isolation goggles laces penetrate into medical isolation goggles lace openings 1 at rear ends of both sides of the pair of personalized medical isolation goggles. High transmittance lenses 3 are embedded in a goggles frame at a front end of the pair of personalized medical isolation goggles. Both sides of a medical isolation goggles frame body 4 of the pair of personalized medical isolation goggles are provided with several air holes 2, where the air holes 2 each have a diameter of 2 mm. Filter cotton is placed in a filter cotton placement bracket 6 at the periphery of the air holes 2, and finally the pair of finished personalized medical isolation goggles is obtained. Then, the pair of finished personalized medical isolation goggles is packaged and undergoes express delivery.

In this example, the medical isolation goggles lace is an elastic band, and a buckle is arranged at a joint of the elastic band, thereby facilitating the adjustment of tightness. The air holes 2 enable the personalized medical isolation goggles to form airflow circulation when in use. This improves the breathability of the medical isolation goggles and meets the technical requirements of the personal eye protection standard. The curved nose bracket 5 highly fits the user's face, which improves use comfort.

In this example, the medical isolation goggles matrix model is established by three-dimensional scanning of the basic tester, and the user's point cloud data is obtained by photographing or three-dimensionally scanning the user. The medical isolation goggles matrix model and the user's point cloud data are imported into the 3D software for Boolean operations to obtain the personalized medical isolation goggles model conforming to the user's face. Finally, the personalized medical isolation goggles model is imported into the 3D printer for quick printing and manufacturing. Small-batch rapid production can be performed after data merging, and a large number of processes and costs are reduced in the production cycle. Through the 3D printing technology, emergency protective equipment can be quickly manufactured and the problem of shortage of medical protective equipment can be solved. This example provides a pair of medical isolation goggles with high personalized fitness and high breathability for patients with eye diseases such as conjunctivitis, virus-susceptible patients, front-line clinical medical workers and related workers, and the compression damage to the face caused by the wearing of the medical isolation goggles for a long time is reduced in terms of fitness and comfort.

Specific examples are applied in this specification to describe the principle and implementations of the present invention. The description of the foregoing examples is only used for facilitating understanding of the method and the core idea of the present invention. Besides, for those of ordinary skills in the art, there may be changes in specific implementations and application scope in accordance with the idea of the present invention. In conclusion, the content of the present specification shall not be construed as a limitation to the present invention.

Thus, while there have been shown, described and pointed out fundamental novel features of the invention as applied to a preferred embodiment thereof, it will be understood that various omissions and substitutions and changes in the form and details of the methods described and the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method for preparing personalized medical isolation goggles by three-dimensional (3D) printing, comprising the following steps:

S1: establishing a medical isolation goggles matrix model by performing 3D scanning on a basic tester to obtain point cloud data from front and side faces of the face of the basic tester, and performing 3D design on the obtained data to obtain the medical isolation goggles matrix model;

S2: acquiring facial data of a user destined to wear the personalized medical isolation goggles by photographing the user or performing 3D scanning on the user to obtain point cloud data from front and side faces of the user;

S3: establishing a personalized medical isolation goggles model by importing the point cloud data of the medical isolation goggles matrix model in said S1 and the point cloud data of the user in said S2 into 3D software for Boolean operations, and forming, by merging and cutting, a personalized medical isolation goggles model conforming to the face of the user; and S4: performing additive manufacturing by importing the personalized medical isolation goggles model into slice software matched with a 3D printer to perform 3D model slicing, generating a print format file which can be identified by the 3D printer, and inputting the print format file into the 3D printer to print the personalized medical isolation goggles model to obtain a pair of personalized medical isolation goggles.

2. The method for preparing personalized medical isolation goggles by 3D printing according to claim 1, wherein during 3D scanning, the basic tester sits down naturally with eyes closed, high-precision 3D data of the face of the basic tester is quickly acquired via a hand-held 3D scanner, and the point cloud data of the face of the basic tester is converted into triangular mesh surface data in software of the 3D scanner.

3. The method for preparing personalized medical isolation goggles by 3D printing according to claim 1, wherein the 3D software is Solid Works or Autodesk Maya.

4. The method for preparing personalized medical isolation goggles by 3D printing according to claim 1, wherein Boolean operations are performed in accordance with the nose, brow ridge and forehead in the scanning data of the user and the medical isolation goggles matrix model.

5. The method for preparing personalized medical isolation goggles by 3D printing according to claim 1, wherein the personalized medical isolation goggles model is saved in "Standard Triangle Language" or "Standard Tessellation Language" (STL) format.

6. The method for preparing personalized medical isolation goggles by 3D printing according to claim 1, wherein 3D printing is performed by a thermoplastic polyurethane (TPU) material and a stereolithography appearance (SLA) technology.

7. The method for preparing personalized medical isolation goggles by 3D printing according to claim 1, further comprising:

S5 post-processing assembly specifically as follows: the pair of personalized medical isolation goggles is cleaned and ground to remove unnecessary supports and post-cured and sterilized, a layer of sponge pad is stuck to a curved nose bracket of the pair of personalized medical isolation goggles, medical isolation goggles laces penetrate into medical isolation goggles lace openings at rear ends of both sides of the pair of personalized medical isolation goggles, high transmittance lenses are embedded in a goggles frame at a front end of the pair of personalized medical isolation goggles, both sides of a medical isolation goggles frame body of the pair of personalized medical isolation goggles are provided with several air holes, filter cotton is placed in a filter cotton placement bracket at the periphery of the air holes, and finally the pair of finished personalized medical isolation goggles is obtained.

8. The method for preparing personalized medical isolation goggles by 3D printing according to claim 7, wherein the medical isolation goggles lace is an elastic band, and a buckle is arranged at a joint of the elastic band.

* * * * *